(12) United States Patent
Druzgala et al.

(10) Patent No.: US 6,784,199 B2
(45) Date of Patent: Aug. 31, 2004

(54) ISOXAZOLIDINE COMPOUNDS USEFUL IN THE TREATMENT OF DIABETES, HYPERLIPIDEMIA, AND ATHEROSCLEROSIS IN MAMMALS

(75) Inventors: Pascal Druzgala, Santa Rosa, CA (US); Peter G. Milner, Los Altos Hills, CA (US)

(73) Assignee: Aryx Therapeutics, Sunnyvale, CA (US)

(*) Notice: Subject to any disclaimer, the term of this patent is extended or adjusted under 35 U.S.C. 154(b) by 38 days.

(21) Appl. No.: 09/961,538

(22) Filed: Sep. 21, 2001

(65) Prior Publication Data

US 2002/0045620 A1 Apr. 18, 2002

Related U.S. Application Data

(60) Provisional application No. 60/234,423, filed on Sep. 21, 2000, and provisional application No. 60/314,792, filed on Aug. 24, 2001.

(51) Int. Cl.[7] ................... A61K 31/423; C07D 413/10
(52) U.S. Cl. ................. 514/375; 514/254.02; 514/340; 514/343; 514/374; 514/375; 514/376; 514/380; 544/405; 546/271.4; 546/276.4; 546/279.1; 548/222; 548/229; 548/236; 548/243
(58) Field of Search .................... 544/405; 546/271.4, 546/276.4, 279.1; 548/222, 229, 236, 243; 514/254.02, 340, 343, 374, 375, 376, 380

(56) References Cited

U.S. PATENT DOCUMENTS

| | | | |
|---|---|---|---|
| 4,287,200 A | 9/1981 | Kawamatsu et al. | 424/270 |
| 4,340,605 A | 7/1982 | Kawamatsu et al. | 424/263 |
| 4,376,777 A | 3/1983 | Kawamatsu et al. | 424/270 |
| 4,438,141 A | 3/1984 | Kawamatsu et al. | 424/248.51 |
| 4,444,779 A | 4/1984 | Kawamatsu et al. | 424/263 |
| 4,461,902 A | 7/1984 | Kawamatsu et al. | 548/183 |
| 4,572,912 A | 2/1986 | Yoshioka et al. | 514/369 |
| 4,687,777 A | 8/1987 | Meguro et al. | 514/342 |
| 4,703,052 A | 10/1987 | Eggler et al. | 514/337 |
| 4,725,610 A | 2/1988 | Meguro et al. | 514/369 |
| 4,873,255 A | 10/1989 | Yoshioka et al. | 514/369 |
| 4,897,393 A | 1/1990 | Iijima et al. | 514/233.8 |
| 4,897,405 A | 1/1990 | Alessi et al. | 514/360 |
| 4,918,091 A | 4/1990 | Cantello et al. | 514/369 |
| 4,948,900 A | 8/1990 | Iijima et al. | 548/183 |
| 5,002,953 A | 3/1991 | Hindley | 514/275 |
| 5,061,717 A | 10/1991 | Clark et al. | 514/342 |
| 5,120,754 A | 6/1992 | Clark et al. | 514/369 |
| 5,132,317 A | 7/1992 | Cantello et al. | 514/369 |
| 5,194,443 A | 3/1993 | Hindley | 514/367 |
| 5,223,522 A | 6/1993 | Clark et al. | 514/369 |
| 5,232,925 A | 8/1993 | Hindley | 514/272 |
| 5,260,445 A | 11/1993 | Hindley | 548/183 |
| 5,480,896 A | 1/1996 | Malamas et al. | 514/364 |
| 5,677,330 A | 10/1997 | Abraham et al. | 514/421 |
| 5,955,616 A | 9/1999 | Ohtani et al. | 548/183 |
| 6,037,359 A | 3/2000 | Shinkai | 514/374 |
| 6,121,288 A | 9/2000 | Matsui et al. | 514/314 |
| 2003/0027798 A1 | 2/2003 | Druzgala et al. | 514/84 |
| 2003/0064972 A1 | 4/2003 | Druzgala et al. | 514/176 |

FOREIGN PATENT DOCUMENTS

| | | |
|---|---|---|
| EP | 0 306 228 A1 | 3/1989 |
| EP | 0 419 035 A1 | 3/1991 |
| EP | 0 528 734 A1 | 2/1993 |
| EP | 0 603 419 A1 | 6/1994 |
| EP | 0 684 242 A1 | 11/1995 |
| EP | 0 801 063 A1 | 10/1997 |
| EP | 0 919 232 A1 | 6/1999 |
| EP | 0 930 299 A1 | 7/1999 |
| EP | 0 953 355 A1 | 11/1999 |
| EP | 0 992 503 A1 | 4/2000 |
| EP | 1 048 659 A1 | 11/2000 |
| ES | 2 154 551 A1 | 4/2001 |
| WO | WO 89/08651 | 9/1989 |
| WO | WO 91/07107 | 5/1991 |
| WO | WO 92/02520 | 2/1992 |
| WO | WO 93/21166 A1 | 10/1993 |
| WO | WO 98/45291 A1 | 10/1998 |
| WO | WO 00/18759 A1 | 4/2000 |
| WO | WO 01/00566 A2 | 1/2001 |
| WO | WO 01/02377 A1 | 1/2001 |
| WO | WO 01/16122 A1 | 3/2001 |
| WO | WO 01/16132 A1 | 3/2001 |
| WO | WO 01/81328 A2 | 11/2001 |
| WO | WO 02/24689 A1 | 3/2002 |
| WO | WO 02/44127 A1 | 6/2002 |

OTHER PUBLICATIONS

Suzuki et al., Chemical Abstracts, vol. 122:174262, 1995.*

Khalil et al., Chemical Abstracts, vol. 110:38850, 1989.*

Cantello, B., et al., "[[ω–(Heterocyclylamino)alkoxy]benzyl]–2,4–thiazolinediones as Potent Antihyperglycemic Agents", *J. Med. Chem.* (1994), 37:3977–3985; XP–001094112; American Chemical Society.

(List continued on next page.)

*Primary Examiner*—Richard L. Raymond
(74) *Attorney, Agent, or Firm*—Saliwanchik, Lloyd & Saliwanchik

(57) ABSTRACT

The subject invention provides pharmaceutical compounds useful in the treatment of Type II diabetes. These compounds are advantageous because they are readily metabolized by the metabolic drug detoxification systems. Particularly, isoxazolidine compounds which have been designed to include esters within the structure of the compounds are provided. This invention is also drawn to methods of treating disorders, such as diabetes, comprising the administration of therapeutically effective compositions comprising compounds which have been designed to be metabolized by serum or intracellular hydrolases and esterases. Pharmaceutical compositions of the isoxazolidine compounds are also taught.

5 Claims, 7 Drawing Sheets

OTHER PUBLICATIONS

Chen, L., et al., "Focused Library Approach for Identification of N–Acylphenylalanines as VCAM/VLA–4 Antagonists", *Bioorg. Med. Chem. Lett.* (2002), 12:1679–1682; XP–002230539; Elsevier Science Ltd.

Database Crossfire Beilstein; Beilstein Registry No.: 6526484; Beilstein Institut zur Foerderung der Chemischen Wissenschaften; XP–002230540; Frankfurt am Main, DE.

Haigh, D., et al., "Non–thiazolidinedione Antihyperglycaemic Agents. Part 3: The effects of stereochemistry on the potency of α–Methoxy–β–phenypropanoic Acids", *Bioorg. Med. Chem.* (1999), 7:821–830; XP–000995637; Elsevier Science Limited.

Henke, B., et al., "N–(2–Benzoylphenyl)–L–tyrosine $PPAR_\gamma$ Agonist. 1. Discovery of a Novel Series of Potent Antihyperglycemic and Antihyperlipidemic Agents", *J. Med. Chem.* (1998), 41:5020–5036; XP–000864731; American Chemical Society.

*Patent Abstracts of Japan* (2001), vol. 2000, No. 19.

Rahbar, S., et al., "Novel Inhibitors of Advanced Glycation Endproducts", *Biochem. Biophys. Reas. Comm.* (1999), 262:651–656; XP–000946146; Academic Press.

Crespi, C., "Higher–throughput screening with human cytochromas P450", *Current Opinion in Drug Discovery & Development*, 1999, pp. 15–19, vol. 2 No. 1., Current Drugs Ltd.

Database CAPLUS 'Online! Chemical Abstracts Service,' Columbus, Ohio, USA; Database Accession No. 127:248106, XP002222346, Torii Pharmaceuticals Co., Ltd., Japan, 1997.

Database CHEMCATS, AsInEx Compound Collection, Moscow, Russia; Accession No. 2001:694380, May 10, 2001; XP002222347.

Database CHEMCATS, Pharma Library Collection, Nanosyn Combinational Synthesis, Inc., Mountain View, CA, USA; Accession No. 2001:54111, May 14, 2001; XP002222348.

Database CHEMCATS, Ambinter Exploratory Library, Paris, France; Accession No. 2002:1116502, Jan. 21, 2002; XP002222349.

Crespi, C.L., et al., "Microtiter Plate Assays for Inhibition of Human, Drug–Metabolizing Cytochromes P450," *Anal. Biochem.* (1997) 248:188–190, Pub: Academic Press.

Favreau, L.V., et al., "Improved Reliability of the Rapid Microtiter Plate Assay Using Recombinant Enzyme in Predicting CYP2D6 Inhibition in Human Liver Microsomes," *Drug Metab. & Dispos.* (1999) 27(4):436–439, Pub: The American Society for Pharmacology & Experimental Therapeutics.

Houston, J.B., "Utility of in vitro Drug Metabolism Data in Predicting in Vivo Metabolic Clearance," *Biochem. Pharmacol.* (1994) 47(9):1469–79; Pub: Elsevier Science Ltd., Great Britain.

Irvine, J.D., et al., "MDCK (Madin–Darby Canine Kidney) Cells: A Tool for Membrane Permeability Screening," *J. Pharm. Sci.* (1999) 88(1):28–33, Pub: American Chemical Society and American Pharmacological Society.

Korzekwa, K.R., et al. "Evaluation of Atypical Cytochrome P450 Kinetics With Two–Substrate Models: Evidence That Multiple Substrates Can Simultaneously Blind to Cytochrome P450 Active Sites," *Biochemistry* (1998) 37:4137–47.

Kostrubsky, V.E., et al., "Effect of Taxol on Cytochrome P450 3A and Acetaminophen Toxicity in Cultured Rat Hepatocytes: Comparison to Dexamethasone," *Toxicol. & Appl. Pharmacol.* (1997) 142:79–86, Article No. TO968023; Pub: Academic Press.

Stewart, B.H., et al., "Comparison of intestinal Permeabilities Determined in Multiple in Vitro and in Situ Models: Relationship to Absorption in Humans," *Pharm. Res.* (1995) 12(5):693–99; Pub: Plenum Publishing Corp.

Swanson, H.I. and Bradfield, C.A., "The AH–Receptor: Genetics, Structure and Function," *Pharmacogenetics* (1993) 3:213–30; Pub: Chapman & Hall.

Tiller, P.R., et al., "Immobilized Human Serum Albumin: Liquid Chromatography/Mass Spectrometry as a Method of Determining Drug–Protein Binding," *Rapid Comm. in Mass Spectrometry* (1995) 9:261–3; Pub: John Wiley & Sons, Ltd.

\* cited by examiner

ISOXAZOLIDINE COMPOUNDS USEFUL IN THE TREATMENT OF DIABETES, HYPERLIPIDEMIA, AND ATHEROSCLEROSIS IN MAMMALS

CROSS REFERENCE TO RELATED APPLICATIONS

This application claims priority to U.S. Provisional Application Ser. No. 60/234,423, filed Sep. 21, 2000; and U.S. Provisional Application Ser. No. 60/314,792, filed Aug. 24, 2001, each of which is hereby incorporated by reference in its entirety, including all tables, formulas, chemical structures, and figures.

BACKGROUND OF THE INVENTION

Diabetes is one of the most prevalent chronic disorders worldwide with significant personal and financial costs for patients and their families, as well as for society. Different types of diabetes exist with distinct etiologies and pathogeneses. For example, diabetes mellitus is a disorder of carbohydrate metabolism, characterized by hyperglycemia and glycosuria and resulting from inadequate production or utilization of insulin.

Noninsulin-dependent diabetes mellitus (NIDDM), often referred to as Type II diabetes, is a form of diabetes which occurs predominantly in adults who produce adequate levels of insulin but who have a defect in insulin-mediated utilization and metabolism of glucose in peripheral tissues. Overt NIDDM is characterized by three major metabolic abnormalities: resistance to insulin-mediated glucose disposal, impairment of nutrient-stimulated insulin secretion, and overproduction of glucose by the liver. It has been shown that for some people with diabetes a genetic predisposition results from a mutation in the gene(s) coding for insulin and/or the insulin receptor and/or insulin-mediated signal transduction factor(s), thereby resulting in ineffective insulin and/or insulin-mediated effects thus impairing the utilization or metabolism of glucose.

For people with Type II diabetes, insulin secretion is often enhanced, presumably to compensate for insulin resistance. Eventually, however, the β-cells fail to maintain sufficient insulin secretion to compensate for the insulin resistance. Mechanisms responsible for the β-cell failure have not been identified, but may be related to the chronic demands placed on the β-cells by peripheral insulin resistance and/or to the effects of hyperglycemia. The β-cell failure could also occur as an independent, inherent defect in "pre-diabetic" individuals.

NIDDM often develops from certain at risk populations. One such population is individuals with polycystic ovary syndrome (PCOS). PCOS is the most common endocrine disorder in women of reproductive age. This syndrome is characterized by hyperandrogenism and disordered gonadotropin secretion producing oligo- or anovulation. Recent prevalence estimates suggest that 5–10% of women between 18–44 years of age (about 5 million women, according to the 1990 census) have the full-blown syndrome of hyperandrogenism, chronic anovulation, and polycystic ovaries. Despite more than 50 years since its original description, the etiology of the syndrome remains unclear. The biochemical profile, ovarian morphology, and clinical features are non-specific; hence, the diagnosis remains one of exclusion of disorders, such as androgen-secreting tumors, Cushing's Syndrome, and late-onset congenital adrenal hyperplasia. PCOS is associated with profound insulin resistance resulting in substantial hyperinsulinemia. As a result of their insulin resistance, PCOS women are at increased risk to develop NIDDM.

NIDDM also develops from the at risk population of individuals with gestational diabetes mellitus (GDM). Pregnancy normally is associated with progressive resistance to insulin-mediated glucose disposal. In fact, insulin sensitivity is lower during late pregnancy than in nearly all other physiological conditions. The insulin resistance is thought to be mediated in large part by the effects of circulating hormones such as placental lactogen, progesterone, and cortisol, all of which are elevated during pregnancy. In the face of the insulin resistance, pancreatic β-cell responsiveness to glucose normally increases nearly 3-fold by late pregnancy, a response that serves to minimize the effect of insulin resistance on circulating glucose levels. Thus, pregnancy provides a major "stress-test" of the capacity for β-cells to compensate for insulin resistance.

Other populations thought to be at risk for developing NIDDM include persons with Syndrome X; concomitant hyperinsulinemia; insulin resistance characterized by hyperinsulinemia and by failure to respond to exogenous insulin; and abnormal insulin and/or evidence of glucose disorders associated with excess circulating glucocorticoids, growth hormone, catecholamines, glucagon, parathyroid hormone, and other insulin-resistant conditions.

Failure to treat NIDDM can result in mortality due to cardiovascular disease and in other diabetic complications including retinopathy, nephropathy, and peripheral neuropathy. There is a substantial need for a method of treating at risk populations such as those with PCOS and GDM in order to prevent or delay the onset of NIDDM thereby bringing relief of symptoms, improving the quality of life, preventing acute and long-term complications, reducing mortality and treating accompanying disorders of the populations at risk for NIDDM.

For many years, treatment of NIDDM has involved a program aimed at lowering blood sugar with a combination of diet and exercise. Alternatively, treatment of NIDDM can involve oral hypoglycemic agents, such as sulfonylureas alone or in combination with insulin injections. Recently, alpha-glucosidase inhibitors, such as a carboys, have been shown to be effective in reducing the postprandial rise in blood glucose (Lefevre, et al., Drugs 1992;44:29–38). In Europe and Canada another treatment used primarily in obese diabetics is metformin, a biguanide.

Compounds useful in the treatment of the various disorders discussed above, and methods of making the compounds, are known and some of these are disclosed in U.S. Pat. Nos. 5,223,522; 5,132,317; 5,120,754; 5,061,717; 4,897,405; 4,873,255; 4,687,777; 4,572,912; 4,287,200; 5,002,953; 4,340,605; 4,438,141; 4,444,779; 4,461,902; 4,703,052; 4,725,610; 4,897,393; 4,918,091; 4,948,900; 5,194,443; 5,232,925; and 5,260,445; WO 91/07107; WO 92/02520; WO 94/01433; WO 89/08651; and J P Kokai 69383/92. The compounds disclosed in these issued patents and applications are useful as therapeutic agents for the treatment of diabetes, hyperglycemia, hypercholesterolemia, and hyperlipidemia. The teachings of these issued patents are incorporated herein by reference in their entireties.

Drug toxicity is an important consideration in the treatment of humans and animals. Toxic side effects resulting from the administration of drugs include a variety of conditions which range from low grade fever to death. Drug therapy is justified only when the benefits of the treatment protocol outweigh the potential risks associated with the treatment. The factors balanced by the practitioner include the qualitative and quantitative impact of the drug to be used as well as the resulting outcome if the drug is not provided to the individual. Other factors considered include the physical condition of the patient, the disease stage and its history of progression, and any known adverse effects associated with a drug.

Drug elimination is typically the result of metabolic activity upon the drug and the subsequent excretion of the drug from the body. Metabolic activity can take place within the vascular supply and/or within cellular compartments or organs. The liver is a principal site of drug metabolism. The metabolic process can be categorized into synthetic and nonsynthetic reactions. In nonsynthetic reactions, the drug is chemically altered by oxidation, reduction, hydrolysis, or any combination of the aforementioned processes. These processes are collectively referred to as Phase I reactions.

In Phase II reactions, also known as synthetic reactions or conjugations, the parent drug, or intermediate metabolites thereof, are combined with endogenous substrates to yield an addition or conjugation product. Metabolites formed in synthetic reactions are, typically, more polar and biologically inactive. As a result, these metabolites are more easily excreted via the kidneys (in urine) or the liver (in bile). Synthetic reactions include glucuronidation, amino acid conjugation, acetylation, sulfoconjugation, and methylation.

One of the drugs used to treat Type II diabetes is troglitazone. The major side effects of troglitazone are nausea, peripheral edema, and abnormal liver function. Other reported adverse events include dyspnea, headache, thirst, gastrointestinal distress, insomnia, dizziness, incoordination, confusion, fatigue, pruritus, rash, alterations in blood cell counts, changes in serum lipids, acute renal insufficiency, and dryness of the mouth. Additional symptoms that have been reported, for which the relationship to troglitazone is unknown, include palpitations, sensations of hot and cold, swelling of body parts, skin eruption, stroke, and hyperglycemia. Accordingly, new therapeutics for the treatment of diabetes which have fewer, or no, adverse effects (i.e., less toxicity) are desirable.

BRIEF SUMMARY OF THE INVENTION

The subject invention provides materials and methods for the safe and effective treatment of diabetes. In a preferred embodiment, the subject invention provides therapeutic compounds for the treatment of diabetes. The compounds of the subject invention can be used to treat at-risk populations in order to prevent or delay the onset of NIDDM thereby bringing relief of symptoms, improving the quality of life, preventing acute and long-term complications, reducing mortality and treating accompanying disorders.

Advantageously, the subject invention provides compounds which are readily metabolized by the physiological metabolic drug detoxification systems. Specifically, in a preferred embodiment, the therapeutic compounds of the subject invention contain an ester group, which does not detract from the ability of these compounds to provide a therapeutic benefit, but which makes these compounds more susceptible to degradation by hydrolases, particularly serum and/or cytosolic esterases. The subject invention further provides methods of treatment comprising the administration of these compounds to individuals in need of treatment for Type II diabetes.

In a preferred embodiment, the subject invention provides novel isoxazolidinedione derivatives which have hypoglycemic and hypolipidemic actions, and are useful as therapeutic agents in diabetes, hyperlipidemia, and related diseases, particularly in atherosclerosis. The compounds of the present invention are particularly advantageous because of the presence of a carboxylic ester function which gives the compounds improved hypoglycemic and hypolipidemic properties as well as an improved toxicity profile.

Unlike compounds which are metabolized exclusively by oxidative enzymatic mechanisms in the liver, the compounds of the present invention are readily cleaved by esterases, a non-oxidative process, to give polar metabolites which are rapidly and safely eliminated. Esterase metabolism takes place not only in the liver, but in many other tissues as well, thus reducing the bio-burden on the liver and reducing the risks of liver damage.

In a further embodiment, the subject invention pertains to the breakdown products which are formed when the therapeutic compounds of the subject invention are acted upon by esterases. These breakdown products can be used as described herein to monitor the clearance of the therapeutic compounds from a patient.

In yet a further embodiment, the subject invention provides methods for synthesizing the therapeutic compounds of the subject invention.

DETAILED DISCLOSURE OF THE INVENTION

Figure 1:
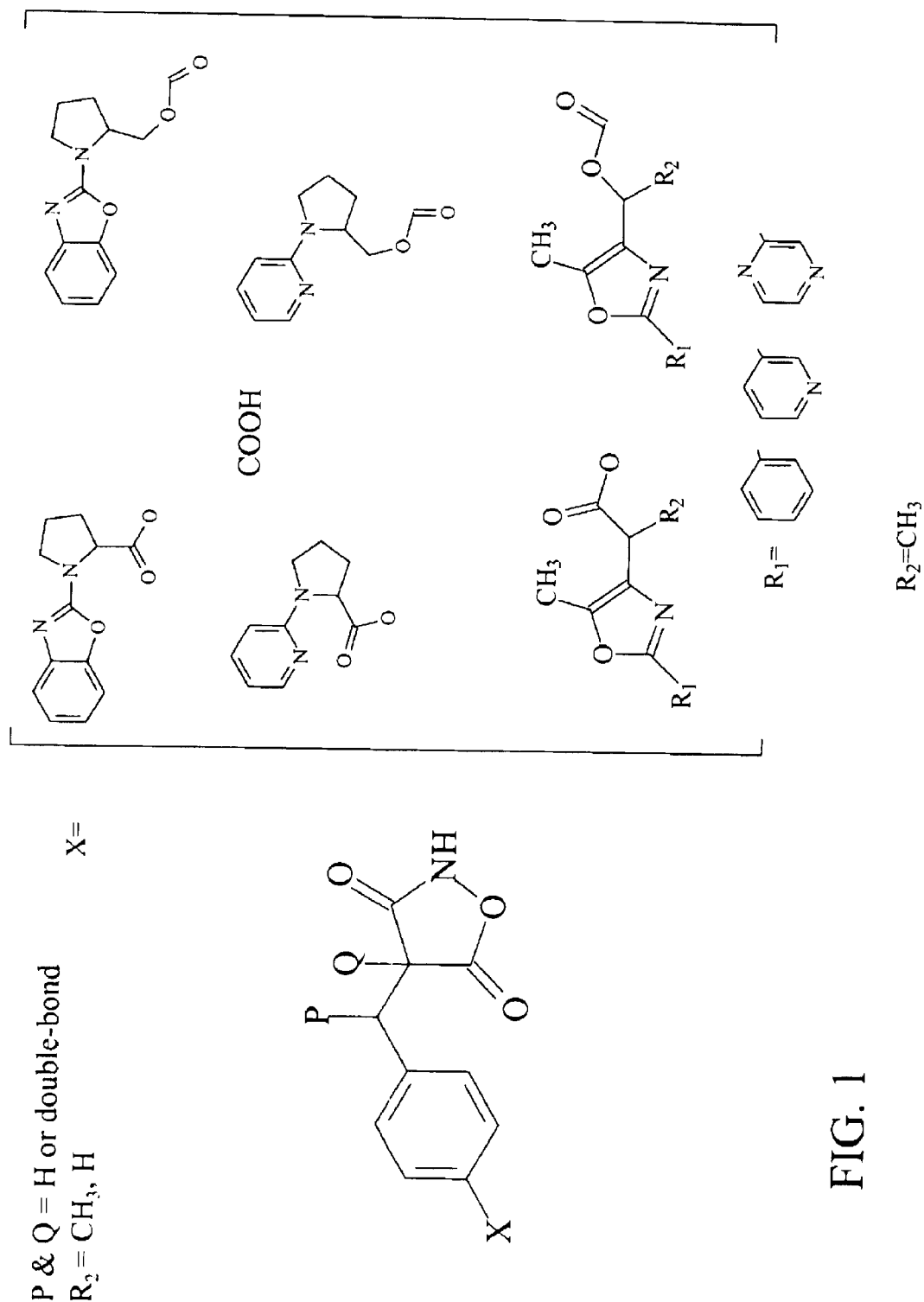
FIG. 1 shows the compounds of the subject invention.

Adverse drug-drug interactions (DDI), elevation of liver function test (LFT) values, and QT prolongation leading to torsades de pointes (TDP) are three major reasons why drug candidates fail to obtain FDA approval. All these causes are, to some extent metabolism-based. A drug that has two metabolic pathways, one oxidative and one non-oxidative, built into its structure is highly desirable in the pharmaceutical industry. An alternate, non-oxidative metabolic pathway provides the treated subject with an alternative drug detoxification pathway (an escape route) when one of the oxidative metabolic pathways becomes saturated or non-functional. While a dual metabolic pathway is necessary in order to provide an escape metabolic route, other features are needed to obtain drugs that are safe regarding DDI, TDP, and LFT elevations.

In addition to having two metabolic pathways, the drug should have a rapid metabolic clearance (short metabolic half-life) so that blood levels of unbound drug do not rise to dangerous levels in cases of DDI at the protein level. Also, if the metabolic half-life of the drug is too long, then the CYP450 system again becomes the main elimination pathway, thus defeating the original purpose of the design. In order to avoid high peak concentrations and rapidly declining blood levels when administered, such a drug should also be administered using a delivery system that produces constant and controllable blood levels over time.

The subject invention provides therapeutically useful and effective compounds and compositions for the treatment of diabetes and a variety of related disorders, such as hyperlipidemia, and atherosclerosis. Various classes of compounds, useful for the treatment of diabetes and related disorders, that can be modified according to the concepts outlined herein include compounds such as the glitazones, thiazolidinediones, and isoxazolidinediones.

The compounds of this invention have one or more of the following characteristics or properties:

1. Compounds of the invention are metabolized both by CYP450 and by a non-oxidative metabolic enzyme or system of enzymes;
2. Compounds of the invention have a short (up to four (4) hours) non-oxidative metabolic half-life;
3. Oral bioavailability of the compounds is consistent with oral administration using standard pharmaceutical oral formulations; however, the compounds, and compositions thereof, can also be administered using any delivery system that produces constant and controllable blood levels over time;
4. Compounds according to the invention contain a hydrolysable bond that can be cleaved non-oxidatively by hydrolytic enzymes;
5. Compounds of the invention can be made using standard techniques of small-scale and large-scale chemical synthesis;
6. The primary metabolite(s) of compound(s) of this invention result(s) from the non-oxidative metabolism of the compound(s);
7. The primary metabolite(s), regardless of the solubility properties of the parent drug, is, or are, soluble in water at physiological pH and have, as compared to the parent compound, a significantly reduced pharmacological activity;
8. The primary metabolite(s), regardless of the electrophysiological properties of the parent drug, has, or have, negligible inhibitory activity at the $IK_R$ (HERG) channel at normal therapeutic concentration of the parent drug in plasma (e.g., the concentration of the metabolite must be at least five times higher than the normal therapeutic concentration of the parent compound before activity at the $IK_R$ channel is observed);
9. Compounds of the invention, as well as the metabolites thereof, do not cause metabolic DDI when co-administered with other drugs;
10. Compounds of the invention, as well as metabolites thereof, do not elevate LFT values when administered alone.

In some embodiments, the subject invention provides compounds have any two of the above-identified characteristics or properties. Other embodiments provide for compounds having at least any three of the above-identified properties or characteristics. In another embodiment, the compounds, and compositions thereof, have any combination of at least four of the above-identified characteristics or properties. Another embodiment provides compounds have any combination of five to 10 of the above-identified characteristics or properties. In a preferred embodiment, the compounds of the invention have all ten characteristics or properties.

In various embodiments, the primary metabolite(s) of the inventive compounds, regardless of the electrophysiological properties of the parent drug, has, or have, negligible inhibitory activity at the $IK_R$ (HERG) channel at normal therapeutic concentrations of the drug in plasma. In other words, the concentration of the metabolite must be at least five times higher than the normal therapeutic concentration of the parent compound before activity at the $IK_R$ channel is observed. Preferably, the concentration of the metabolite must be at least ten times higher than the normal therapeutic concentration of the parent compound before activity at the $IK_R$ channel is observed.

Compounds according to the invention are, primarily, metabolized by endogenous hydrolytic enzymes via hydrolysable bonds engineered into their structures. The primary metabolites resulting from this metabolic pathway are water soluble and do not have, or show a reduced incidence of, DDI when administered with other medications (drugs). Non-limiting examples of hydrolysable bonds that can be incorporated into compounds according to the invention include amide, ester, carbonate, phosphate, sulfate, urea, urethane, glycoside, or other bonds that can be cleaved by hydrolases.

Additional modifications of the compounds disclosed herein can readily be made by those skilled in the art. Thus, analogs, derivatives, and salts of the exemplified compounds are within the scope of the subject invention. With a knowledge of the compounds of the subject invention skilled chemists can use known procedures to synthesize these compounds from available substrates. As used in this application, the terms "analogs" and "derivatives" refer to compounds which are substantially the same as another compound but which may have been modified by, for example, adding additional side groups. The terms "analogs" and "derivatives" as used in this application also may refer to compounds which are substantially the same as another compound but which have atomic or molecular substitutions at certain locations in the compound.

The subject invention further provides novel drugs that are dosed via drug delivery systems that achieve slow release of the drug over an extended period of time. These delivery systems maintain constant drug levels in the target tissue or cells. Such drug delivery systems have been described, for example, in *Remington: The Science and Practice of Pharmacy*, 19$^{th}$ Ed., Mack Publishing Co., Easton, Pa., 1995, pp 1660–1675, which is hereby incorporated by reference in its entirety. Drug delivery systems can take the form of oral dosage forms, parenteral dosage forms, transdermal systems, and targeted delivery systems.

Oral sustained-release dosage forms are commonly based on systems in which the release rate of drug is determined by its diffusion through a water-insoluble polymer. There are basically two types of diffusion devices, namely reservoir devices, in which the drug core is surrounded by a polymeric membrane, and matrix devices, in which dissolved or dispersed drug is distributed uniformly in an inert, polymeric matrix. In actual practice, however, many diffusion devices also rely on some degree of dissolution in order to govern the release rate.

Dissolution systems are based on the fact that drugs with slow dissolution rates inherently produce sustained blood levels. Therefore, it is possible to prepare sustained-release formulations by decreasing the dissolution rate of highly water-soluble drugs. This can be carried out by preparing an appropriate salt or other derivative, by coating the drug with a slowly soluble material, or by incorporating it into a tablet with a slowly soluble carrier.

In actual practice, most of the dissolution systems fall into two categories: encapsulated dissolution systems and matrix dissolution systems. Encapsulated dissolution systems can be prepared either by coating particles or granules of drug with varying thicknesses of slowly soluble polymers or by micro-encapsulation, which can be accomplished by using phase separation, interfacial polymerization, heat fusion, or the solvent evaporation method. The coating materials may be selected from a wide variety of natural and synthetic polymers, depending on the drug to be coated and the release characteristics desired. Matrix dissolution devices are prepared by compressing the drug with a slowly soluble polymer carrier into a tablet form.

In osmotic pressure-controlled drug-delivery systems, osmotic pressure is utilized as the driving force to generate a constant release of drug. Additionally, ion-exchange resins can be used for controlling the rate of release of a drug, which is bound to the resin by prolonged contact of the resin with the drug solution. Drug release from this complex is dependent on the ionic environment within the gastrointestinal tract and the properties of the resin.

Parenteral sustained-release dosage forms most commonly include intramuscular injections, implants for subcutaneous tissues and various body cavities, and transdermal devices. Intramuscular injections can take the form of aqueous solutions of the drug and a thickening agent which increases the viscosity of the medium, resulting in decreased molecular diffusion and localization of the injected volume. In this manner, the absorptive area is reduced and the rate of drug release is controlled. Alternatively, drugs can be complexed either with small molecules such as caffeine or procaine or with macromolecules, e.g., biopolymers such as antibodies and proteins or synthetic polymers, such as methylcellulose or polyvinylpyrrolidone. In the latter case, these formulations frequently take on the form of aqueous suspensions. Drugs which are appreciably lipophilic can be formulated as oil solutions or oil suspensions in which the release rate of the drug is determined by partitioning of the drug into the surrounding aqueous medium. The duration of action obtained from oil suspensions is generally longer than that from oil solutions, because the suspended drug particles must first dissolve in the oil phase before partitioning into the aqueous medium. Water-oil (W/O) emulsions, in which water droplets containing the drug are dispersed uniformly within an external oil phase, can also be used for sustained release. Similar results can be obtained from O/W (reverse) and multiple emulsions.

Implantable devices based on biocompatible polymers allow for both a high degree of control of the duration of drug activity and precision of dosing. In these devices, drug release can be controlled either by diffusion or by activation. In diffusion-type implants, the drug is encapsulated within a compartment that is enclosed by a rate-limiting polymeric membrane. The drug reservoir may contain either drug particles or a dispersion (or a solution) of solid drug in a liquid or a solid-type dispersing medium. The polymeric membrane may be fabricated from a homogeneous or a heterogeneous non-porous polymeric material or a microporous or semi-permeable membrane. The encapsulation of the drug reservoir inside the polymeric membrane may be accomplished by molding, encapsulation, microencapsulation or other techniques. Alternatively, the drug reservoir is formed by the homogeneous dispersion of drug particles throughout a lipophilic or hydrophilic polymer matrix. The dispersion of the drug particles in the polymer matrix may be accomplished by blending the drug with a viscous liquid polymer or a semi-solid polymer at room temperature, followed by crosslinking of the polymer, or by mixing of the drug particles with a melted polymer at an elevated temperature. It can also be fabricated by dissolving the drug particles and/or the polymer in an organic solvent followed by mixing and evaporation of the solvent in a mold at an elevated temperature or under vacuum.

In microreservoir dissolution-controlled drug delivery, the drug reservoir, which is a suspension of drug particles in an aqueous solution of a water-miscible polymer, forms a homogeneous dispersion of a multitude of discrete, unleachable, microscopic drug reservoirs in a polymer matrix. The microdispersion may be generated by using a high-energy dispersing technique. Release of the drug from this type of drug delivery device follows either an interfacial partition or a matrix diffusion-controlled process.

In activation-type implants, the drug is released from the semi-permeable reservoir in solution form at a controlled rate under an osmotic pressure gradient. Implantable drug-delivery devices can also be activated by vapor pressure, magnetic forces, ultrasound, or hydrolysis.

Transdermal systems for the controlled systemic delivery of drugs are based on several technologies. In membrane-moderated systems, the drug reservoir is totally encapsulated in a shallow compartment molded from a drug-impermeable backing and a rate-controlling microporous or non-porous polymeric membrane through which the drug molecules are released. On the external surface of the membrane, a thin layer of drug-compatible, hypoallergenic adhesive polymer may be applied to achieve an intimate contact of the transdermal system with the skin. The rate of drug release from this type of delivery system can be tailored by varying the polymer composition, permeability coefficient or thickness of the rate-limiting membrane and adhesive.

In adhesive diffusion-controlled systems, the drug reservoir is formulated by directly dispersing the drug in an adhesive polymer and then spreading the medicated adhesive, by solvent casting, onto a flat sheet of drug-impermeable backing membrane to form a thin drug reservoir layer. On top of the drug-reservoir layer, layers of non-medicated, rate controlling adhesive polymer of constant thickness are applied to produce an adhesive diffusion-controlled drug-delivery system.

In matrix dispersion systems, the drug reservoir is formed by homogeneously dispersing the drug in a hydrophilic or lipophilic polymer matrix. The medicated polymer is then molded into a disc with a defined surface area and controlled thickness. The disc is then glued to an occlusive baseplate in a compartment fabricated from a drug-impermeable backing. The adhesive polymer is spread along the circumference to form a strip of adhesive rim around the medicated disc. In microreservoir systems, the drug reservoir is formed by first suspending the drug particles in an aqueous solution of a water-soluble polymer and then dispersing homogeneously, in a lipophilic polymer, by high-shear mechanical forces to form a large number of unleachable, microscopic spheres of drug reservoirs. This thermodynamically unstable system is stabilized by crosslinking the polymer in situ, which produces a medicated polymer disk with a constant surface area and a fixed thickness.

Targeted delivery systems include, but are not limited to, colloidal systems such as nanoparticles, microcapsules, nanocapsules, macromolecular complexes, polymeric beads, microspheres, and liposomes. Targeted delivery systems can also include resealed erythrocytes and other immunologically-based systems. The latter may include drug/antibody complexes, antibody-targeted enzymatically-activated prodrug systems, and drugs linked covalently to antibodies.

The invention also provides methods of producing these compounds.

It is another aspect of this invention to provide protocols by which these conditions can be tested. These protocols include in vitro and in vivo tests that have been designed to: 1) ensure that the novel compound is metabolized both by CYP450 and by hydrolytic enzymes; 2) that the non-oxidative half-life of the parent drug is no more than a certain value when compared to an internal standard (in preferred embodiments, less than about four hours); 3) that the primary metabolite of the parent drug is the result of non-oxidative metabolism; 4) that the primary metabolite of the parent drug (regardless of the solubility properties of the parent drug) is water soluble; 5) that the primary metabolite of the parent drug (regardless of the electrophysiological properties of the parent drug) has negligible inhibitory properties toward $IK_R$ channel at concentrations similar to therapeutic concentration of the parent drug; 6) that the novel compound (regardless of its properties) does not cause metabolic DDI when co-administered with other drugs; and 7) that the novel compound does not cause hepatic toxicity in primary human hepatocytes.

The subject invention provides materials and methods for the treatment of non-insulin dependent diabetes mellitus (NIDDM), hyperlipidemia, hypercholesterolemia, and atherosclerosis. Advantageously, the therapeutic compounds of the subject invention are stable in storage but have a shorter half-life in the physiological environment than other drugs which are available for treatment of diabetes; therefore, the compounds of the subject invention can be used with a lower incidence of side effects and toxicity, especially in patients having elevated liver function or compromised liver function.

In a preferred embodiment of the subject invention, therapeutic compounds are provided which are useful in the treatment of diabetes, hyperlipidemia, hypercholesterolemia, and atherosclerosis and which contain an ester group which is acted upon by esterases thereby breaking down the compound and facilitating its efficient removal from the treated individual. In a preferred embodiment, the therapeutic compounds are metabolized by non-oxidative systems and are exemplified by the compound of Formula I.

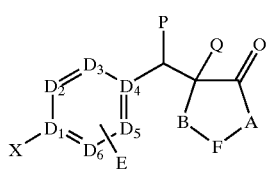

Formula I

For compounds of Formula I:
A, B, and F may be the same or different and are $CH_2$, CO, N, NO, NH, $SO_{0-2}$, O;

$D_1$–$D_6$ can be the same or different and are CH, N, S, or O;

E can be a substituent attached to one or more of the atoms located at $D_1$–$D_6$;

P and Q can be a double bond; or

P, Q, and E can be the same or different and are a moiety selected from the group consisting of H, $C_{1-10}$ alkyl, substituted alkyl groups, substituted or unsubstituted carboxylic acids, substituted or unsubstituted carboxylic esters, halogen, carboxyl, hydroxyl, phosphate, phosphonate, aryl, CN, OH, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which maybe, optionally, substituted with a moiety selected from the group consisting of $C_{1-6}$ alkyl, halogen, OH, $NH_2$, CN, $NO_2$, COOH, or $SO_{2-4}$. Exemplary heterocyclic groups include, but are not limited to, morpholine, triazole, imidazole, pyrrolidine, piperidine, piperazine, pyrrole, dihydropyridine, aziridine, thiazolidine, thiazoline, thiadiazolidine or thiadiazoline.

Substituted carboxylic acids, substituted carboxylic esters, and substituted alkyl groups can be substituted at any available position with a moiety selected from the group consisting of $C_{1-10}$ alkyl, halogen, CN, OH, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which maybe, optionally, substituted with a moiety selected from the group consisting of $C_{1-6}$ alkyl, halogen, OH, $NH_2$, CN, $NO_2$, COOH, or $SO_{2-4}$. Exemplary heterocyclic groups include, but are not limited to, morpholine, triazole, imidazole, pyrrolidine, piperidine, piperazine, pyrrole, dihydropyridine, aziridine, thiazolidine, thiazoline, thiadiazolidine, and thiadiazoline.

X is —OH, —COOH, or a substituted carboxylic group having the carboxyl moiety OOC— or COO— directly attached to the phenyl ring of the compound of Formula I. The carboxylic acid group can be substituted with a moiety selected from the group consisting of alkyloxycarbonyl, alkylcarbonyloxy, aryloxycarbonyl, arylcarbonyloxy, heteroalkyloxycarbonyl, heteroalkylcarbonyloxy, heteroaryl-oxycarbonyl, and heteroarylcarbonyloxy each of which is, optionally, substituted with $C_{1-10}$ alkyl, CN, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$. In other embodiments, the substituted carboxylic group can be substituted with a moiety selected from the group consisting of $C_{1-10}$ alkyl, CN, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$. Exemplary heterocyclic groups include, but are not limited to, morpholine, triazole, imidazole, pyrrolidine, piperidine, piperazine, pyrrole, dihydropyridine, aziridine, thiazolidine, thiazoline, thiadiazolidine, and thiadiazoline.

In one exemplary embodiment, compounds of the invention have the following moieties: A is NH; F is O; B is C=O; P and Q are a double bond or H; $D_1$–$D_6$ are C (carbon), E is hydrogen; X is selected from the group consisting of: COOH, OH,

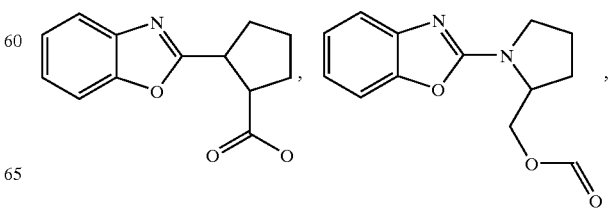

-continued

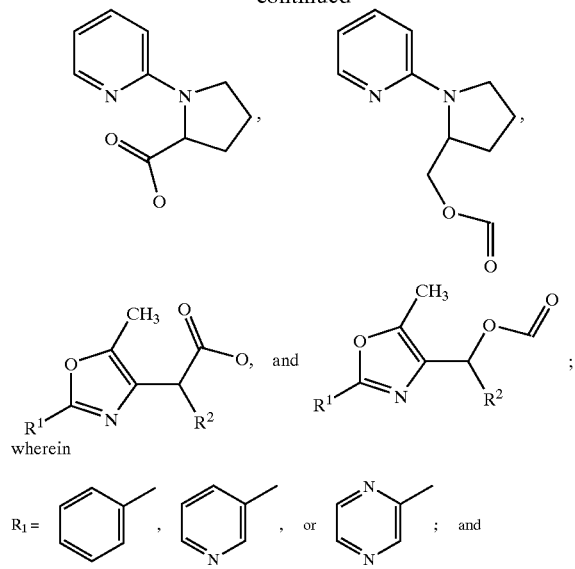

wherein $R_2$ is $CH_3$ or H.

Unlike compounds which are metabolized exclusively by oxidative enzymatic mechanisms in the liver, the compounds of the present invention are readily cleaved by esterases, a non-oxidative process, to give polar metabolites which are rapidly and safely eliminated. Esterase metabolism takes place not only in the liver, but in many other tissues as well, thus reducing the bio-burden on the liver and reducing the risks of liver damage.

A further aspect of the subject invention pertains to the breakdown products which are produced when the therapeutic compounds of the subject invention are acted upon by esterases. The presence of these breakdown products in the urine or serum can be used to monitor the rate of clearance of the therapeutic compound from a patient.

The subject invention further provides methods of synthesizing the unique and advantageous therapeutic compounds of the subject invention. Particularly, methods of producing less toxic therapeutic agents comprising introducing ester groups into therapeutic agents (target drugs) are taught. The ester linkage may be introduced into the compound at a site which is convenient in the manufacturing process for the target drug. Additionally, the sensitivity of the ester linkage may be manipulated by the addition of side groups which hinder or promote the hydrolytic activity of the hydrolases or esterases responsible for cleaving the drug at the ester locus. Methods of adding such side groups, as well as the side groups themselves, are well known to the skilled artisan and can be readily carried out utilizing the guidance provided herein.

The subject invention further provides methods of treating disorders, such as diabetes comprising the administration of a therapeutically effective amount of the compounds of the subject invention to an individual in need of treatment. Accordingly, the subject invention provides esterified isoxazolidine compounds and pharmaceutical compositions of these esterified compounds.

The compounds of this invention have therapeutic properties similar to those of the unmodified parent compounds. Accordingly, dosage rates and routes of administration of the disclosed compounds are similar to those already used in the art and known to the skilled artisan (see, for example, *Physicians' Desk Reference*, 54th Ed., Medical Economics Company, Montvale, N.J., 2000).

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention are formulated such that an effective amount of the bioactive compound(s) is combined with a suitable carrier in order to facilitate effective administration of the composition.

In accordance with the subject invention, pharmaceutical compositions are provided which comprise, as an active ingredient, an effective amount of one or more of the compounds and one or more non-toxic, pharmaceutically acceptable carriers or diluents. Examples of such carriers for use in the invention include ethanol, dimethyl sulfoxide, glycerol, silica, alumina, starch, and equivalent carriers and diluents.

Further, acceptable carriers can be either solid or liquid. Solid form preparations include powders, tablets, pills, capsules, cachets, suppositories and dispersible granules. A solid carrier can be one or more substances which may act as diluents, flavoring agents, solubilizers, lubricants, suspending agents, binders, preservatives, tablet disintegrating agents or encapsulating materials.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid based preparation or formulated to be incorporated into solid food products, chewing gums, or lozenges.

The term "individual(s)" is defined as a single mammal to which is administered a compound of the present invention. The mammal may be, for example a mouse, rat, pig, horse, rabbit, goat, pig, cow, cat, dog, or human. In a preferred embodiment, the individual is a human.

Specifically, exemplified herein are isoxazolidine compounds which are useful as therapeutic agents for the treatment of diabetes. Specifically exemplified herein are isoxalidinedione analogs which are useful in the treatment of NIDDM and related diseases such as hyperlipidemia and atherosclerosis. Modifications of the above compounds, especially modifications on the X-moiety, can readily be made by those skilled in the art having the benefit of the current disclosure without altering the therapeutic properties of the compounds. Thus, analogs and derivatives of the exemplified compounds are within the scope of the present invention.

The subject invention also provides procedures for the synthesis of the therapeutic compounds of interest. An exemplary reaction scheme is provided in FIGS. 2–8. Exemplary compounds are shown in FIG. 1. For the compounds of FIG. 1, P and Q may be H or a double bond and $R_2$ may be $CH_3$ or H.

Modifications of the compounds disclosed herein can readily be made by those skilled in the art. Thus, analogs, derivatives, and salts of the exemplified compounds are within the scope of the subject invention. With a knowledge of the compounds of the subject invention, and their structures, skilled chemists can use known procedures to synthesize these compounds from available substrates.

As used in this application, the terms "analogs" and "derivatives" refer to compounds which are substantially the same as another compound but which may have been modified by, for example, adding additional side groups. The terms "analogs" and "derivatives" as used in this application also may refer to compounds which are substantially the same as another compound but which have atomic or molecular substitutions at certain locations in the compound.

Analogs or derivatives of the exemplified compounds can be readily prepared using commonly known, standard reactions. These standard reactions include, but are not limited to, hydrogenation, methylation, acetylation, and acidification reactions. For example, new salts within the scope of the invention can be made by adding mineral acids, e.g., HCl, $H_2SO_4$, etc., or strong organic acids, e.g., formic, oxalic, etc., in appropriate amounts to form the acid addition salt of the parent compound or its derivative. Also, synthesis type reactions may be used pursuant to known procedures to add or modify various groups in the exemplified compounds to produce other compounds within the scope of the invention.

Figure 2:
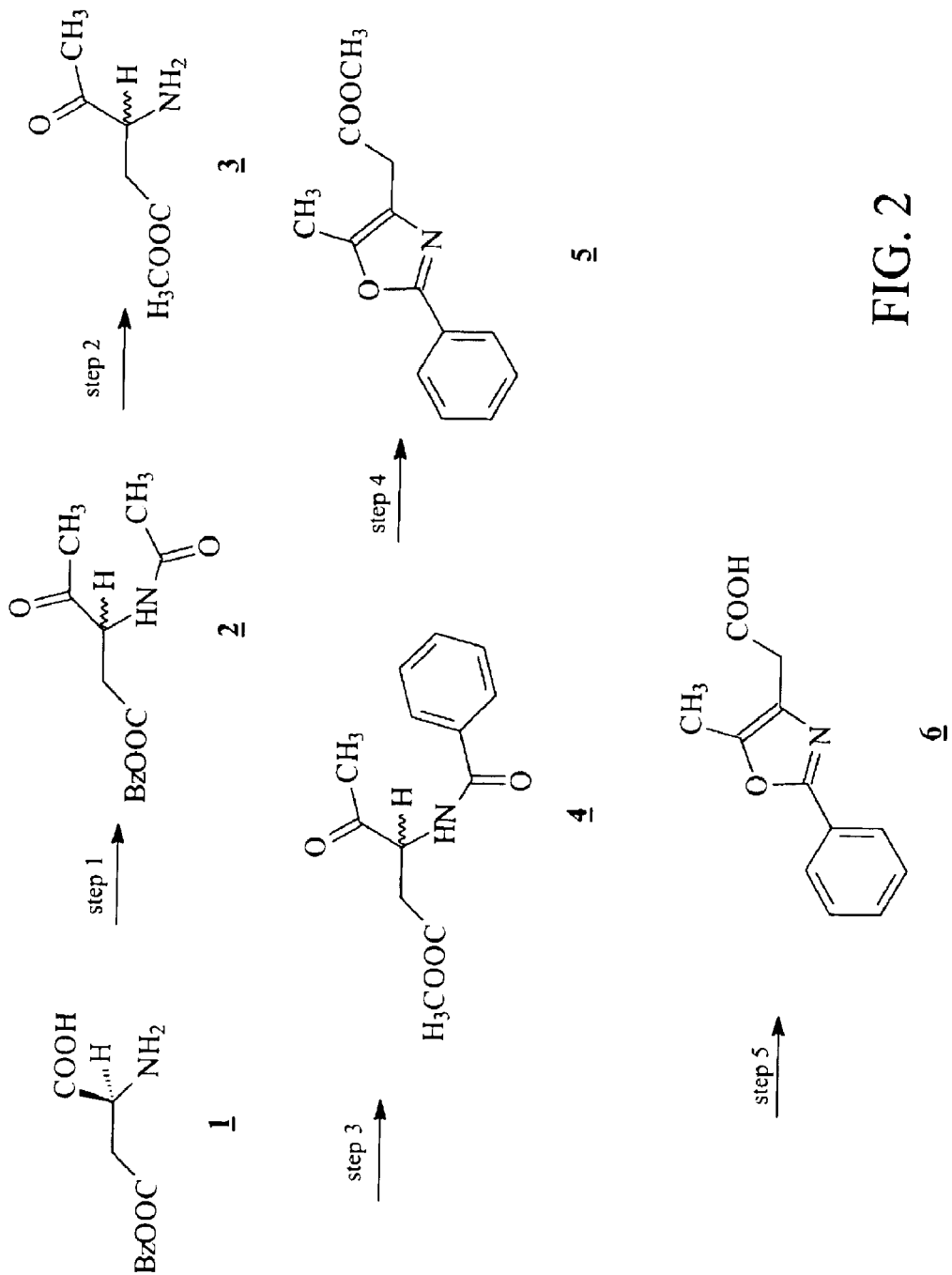
FIGS. 2–8 show a synthesis scheme to produce compounds of the subject invention.
Figure 3:
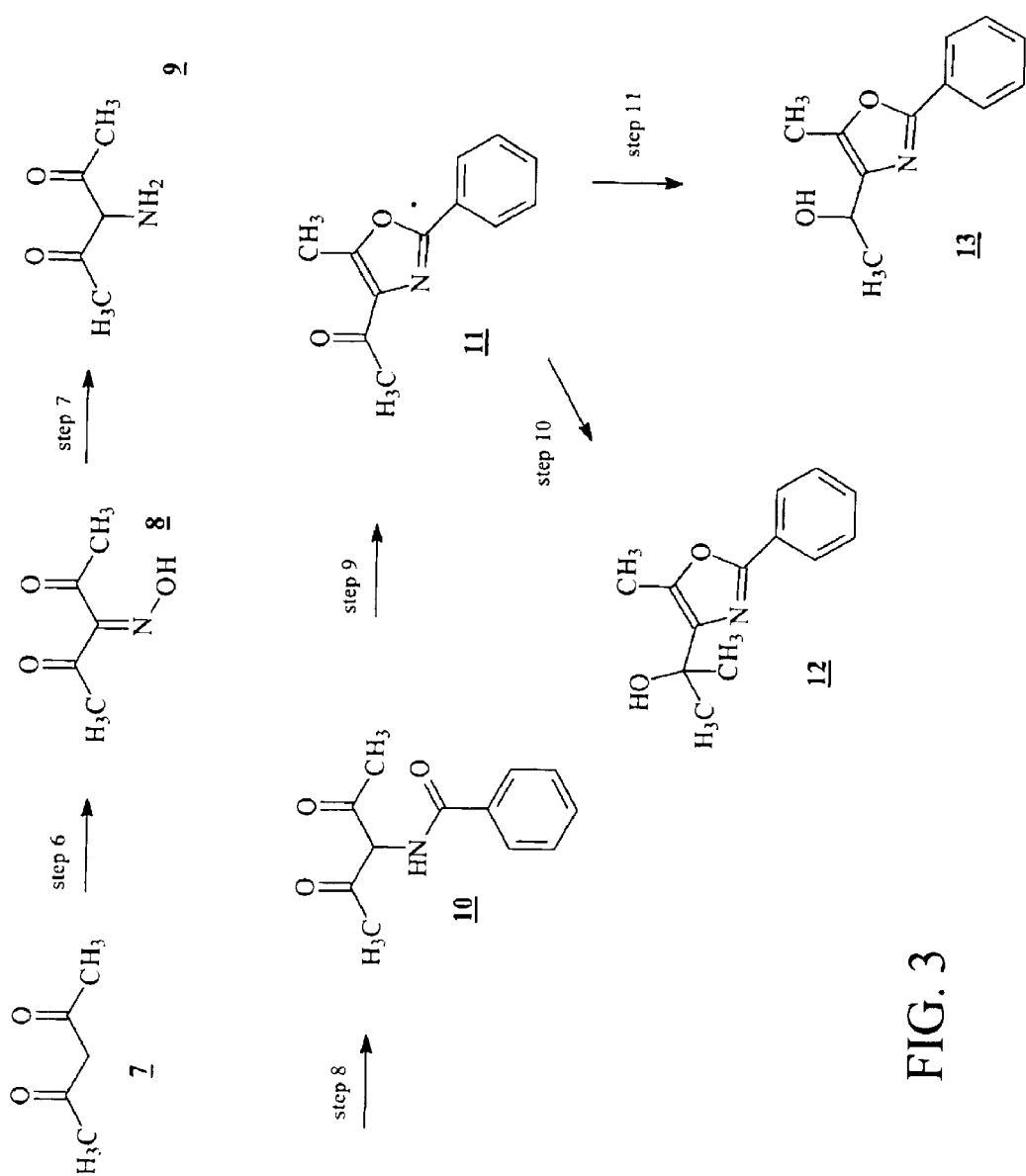
Figure 4:
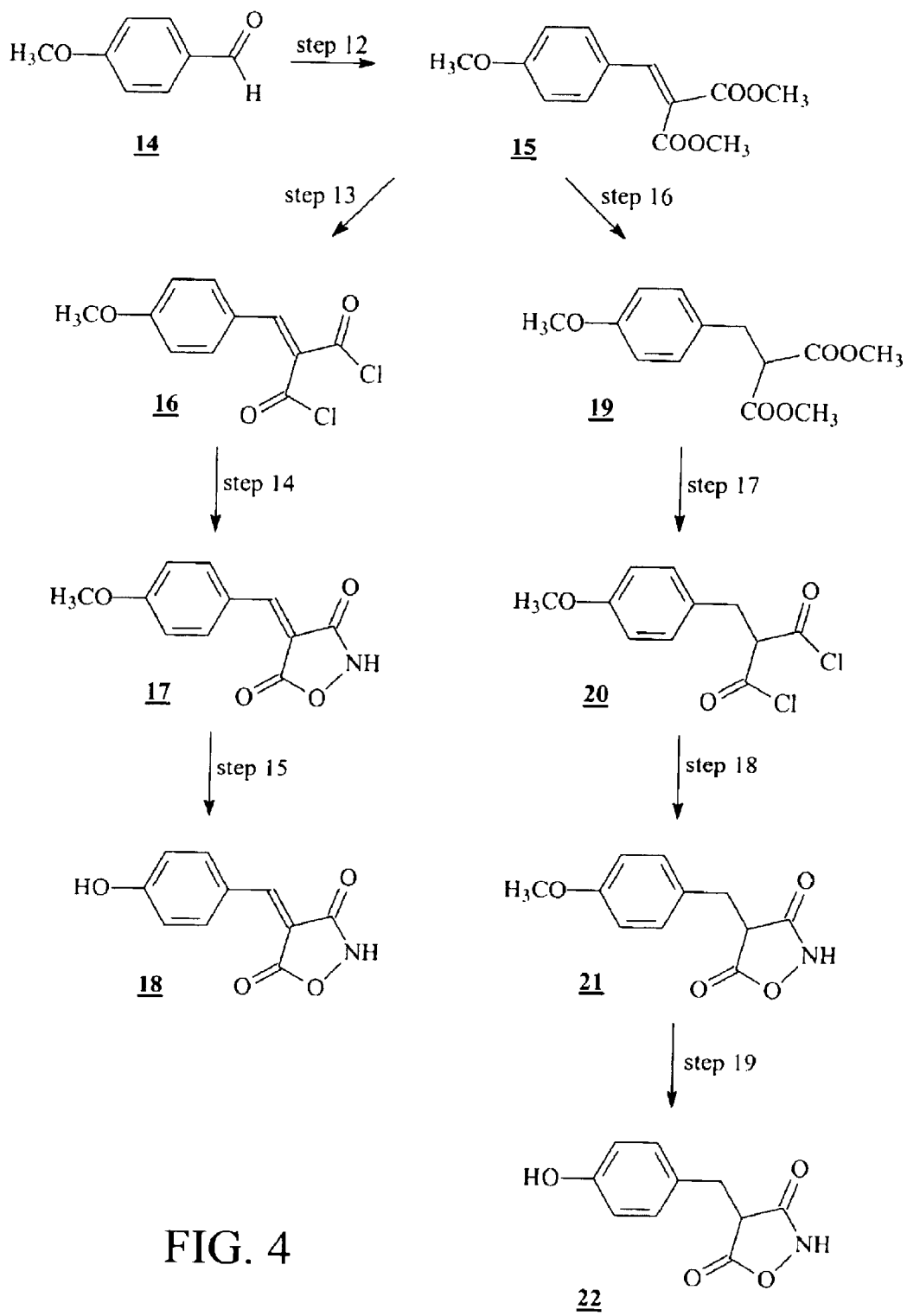
Figure 5:
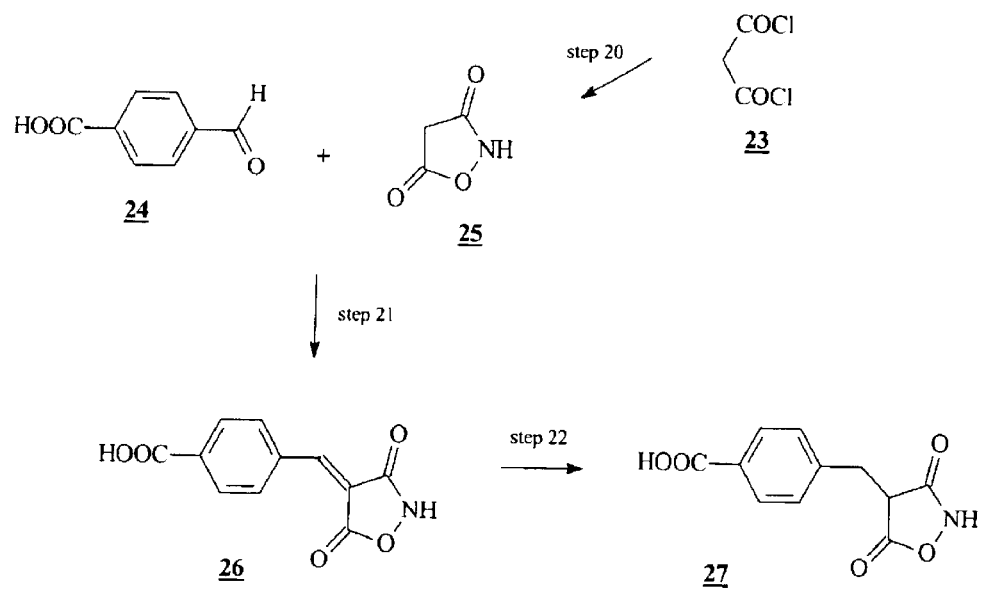
Figure 6:
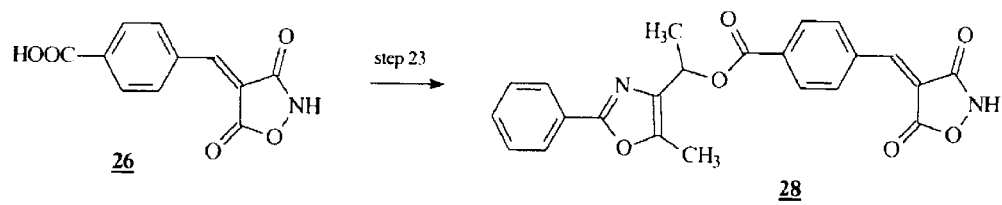
Figure 6:
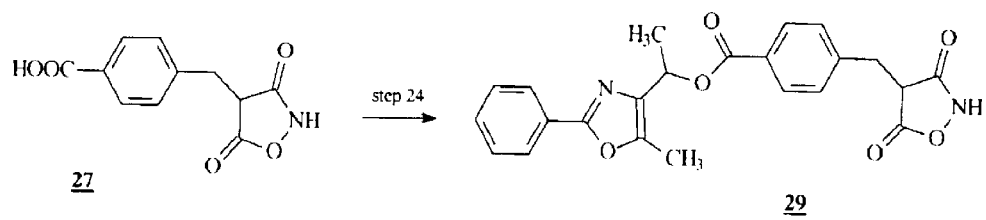
Figure 7:
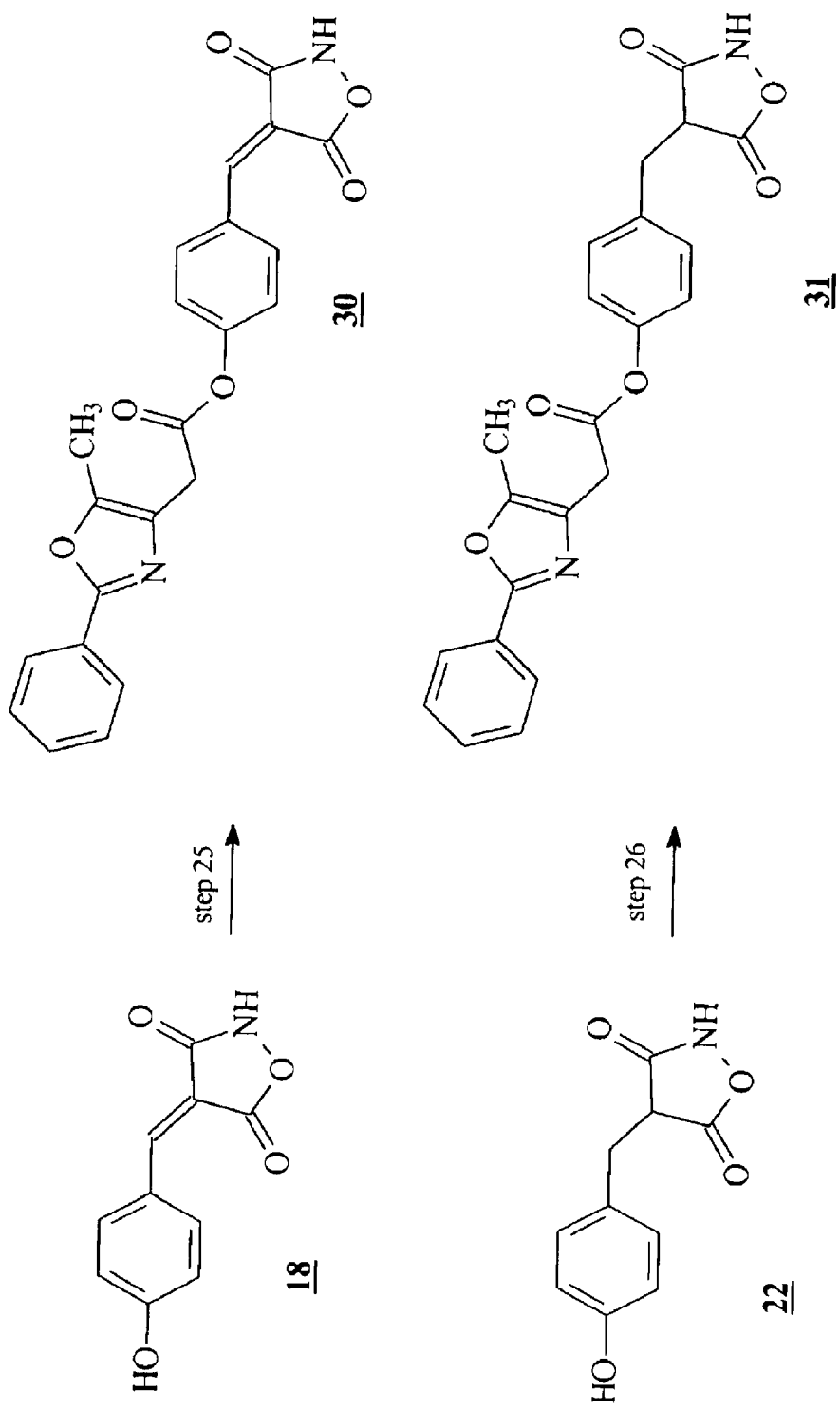
Figure 8:
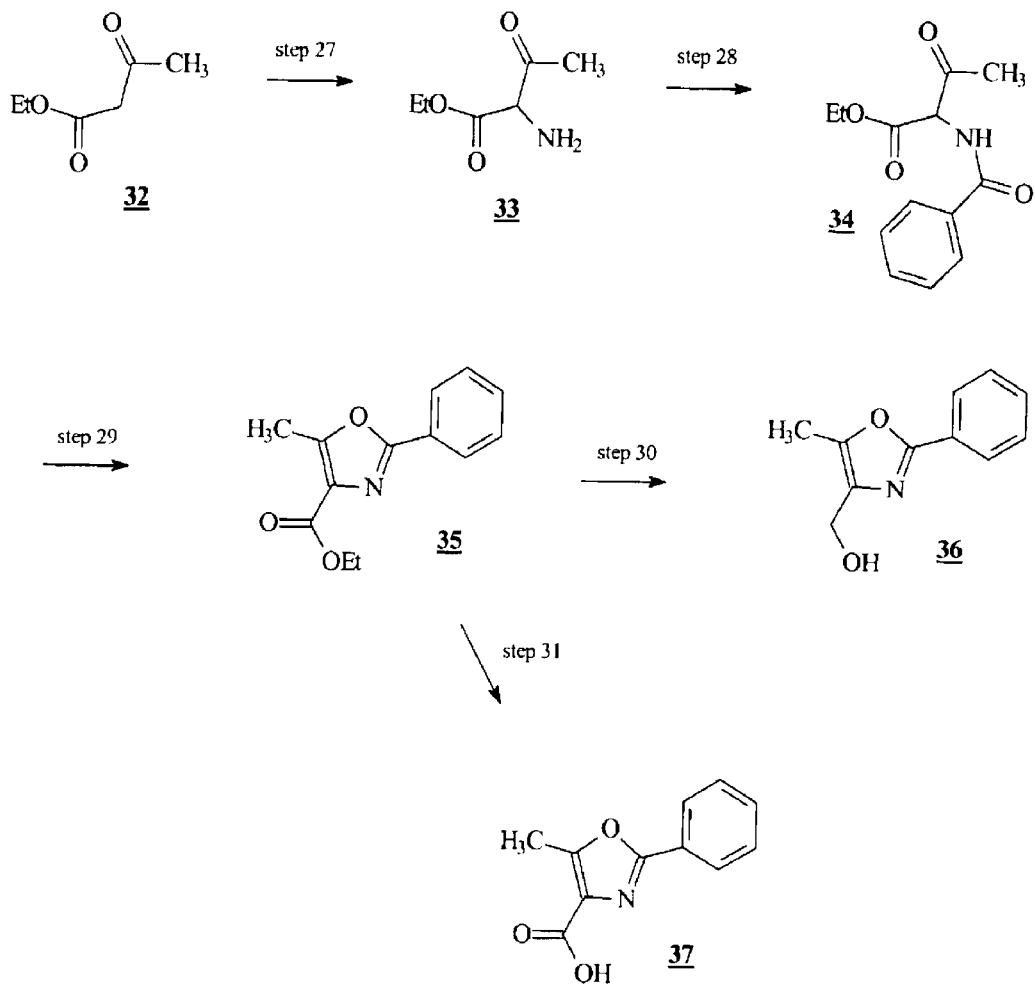

A further aspect of the subject invention provides procedures for synthesizing the therapeutic compounds of interest. An exemplary synthesis scheme is shown in FIGS. 2–4. In step 1, β-benzyl aspartate is suspended in triethylamine and acetic anhydride is added slowly at 0° C. with stirring. A catalytic amount of DMAP is then added under ice-cooling. The mixture is stirred overnight at room temperature and then ice-water is added. The pH is brought up to 9.0 with KOH solution and the product is extracted with ethyl acetate, dried, and concentrated.

In step 2, the acetamide group and the benzyl ester are cleaved with 6N HCl at reflux for 2 hours. The resulting amino acid is then isolated, dried, and then dissolved in a solution of thionyl chloride in methanol. After refluxing for 4 hours, the resulting methyl ester 3 is obtained.

In step 3, the amine compound 3 is suspended in dichloromethane and benzoyl chloride and triethylamine are added under ice-cooling. After stirring for 5 hours at room temperature, the product is washed with sodium bicarbonate solution, dried, and evaporated to give the benzamide 4.

In step 4, the oxazole 5 is formed by dissolving compound 4 in anhydrous ethyl acetate and treating with a catalytic amount of sulfuric acid for 3 hours at 90° C. The product is isolated as usual.

In step 5, the carboxylic acid 6 is obtained by treating 5 with 1 equivalent amount of lithium hydroxide in methanol/water.

Steps 6 and 7 can be combined in a one-pot reaction as follows: Acetylacetone 7 (1.5 mol) is dissolved in 450 ml of glacial acetic acid and the solution is cooled to 5° C. Sodium nitrite (1.5 mol in 150 ml of water) is added slowly so that the temperature stays between 5 and 7° C. Keep stirring for 4 hours at room temperature then add zinc powder (3 mol) portionwise under ice-cooling. Keep stirring at room temperature until the reaction is over and then collect the product 9 by filtration. Dry thoroughly.

Steps 8 and 9 proceed as described before. The amine 9 reacts with benzoyl chloride in dichloromethane in the presence of triethylamine in order to give the benzamide 10. The oxazole 11 is then obtained by cyclization with a catalytic amount of sulfuric acid at reflux in anhydrous ethyl acetate.

In step 10, treating the ketone 11 with 1 equivalent of methyl magnesium iodide in tetrahydrofuran at −40° C. gives the tertiary alcohol 12.

In step 11, the ketone 11 is reduced to the secondary alcohol 13 with sodium borohydride in methanol.

In step 12, p-methoxybenzaldehyde 14 reacts with dimethyl malonate in methanol with a catalytic amount of piperidinium benzoate, giving the benzylidene product 15.

In step 13, the benzylidene 15 is hydrolyzed in methanol/NaOH/water and then is acidified with dilute HCl to give the diacid. The diacid in turn reacts with thionyl chloride to give the acid chloride 16.

In step 14, the acid chloride 16 is dissolved in dichloromethane and triethylamine. Hydroxylamine hydrochloride is added under ice-cooling, giving the isoxazolidine 17.

In step 15, the methoxy-group in compound 17 is cleaved readily by boron tribromide, yielding the phenolic compound 18.

In step 16, the benzylidene compound 15 is reduced by magnesium powder in ethanol, giving dimethyl 4-methoxybenzylmalonate 19.

In steps 17, 18, and 19, compound 19 undergoes a similar sequence of reactions as in steps 13, 14, and 15, i.e., hydrolysis with NaOH/methanol/water and subsequent reaction with thionyl chloride to give the acid chloride 20. Compound 20 in turn reacts with hydroxylamine hydrochloride in dichloromethane and triethylamine to give 21. Finally, cleavage of the ether function with boron tribromide yields the phenolic compound 22.

In step 21, p-carboxybenzaldehyde 24 reacts with 2,4-isoxalolidinedione 25 (made from malonyl chloride and hydroxylamine, step 20) in THF in the presence of piperidinium benzoate to give the benzylidene 26.

In step 22, compound 26 is reduced with magnesium powder in ethanol to give 3-(4-carboxybenzyl)-isoxazolidine-2,4-dione 27.

In step 23, the carboxylic acid 26 reacts with the secondary alcohol 13 in dichloromethane in the presence of 1 equivalent amount of dicyclohexylcarbodiimide (DCC) and 4-dimethylaminopyridine (DMAP), giving the ester 28.

The same reaction takes place in step 24 between compounds 27 and 13, giving the ester 29.

Compounds 28 and 29 are among the group of preferred isoxazolidinedione analogs that have therapeutic properties against NIDDM and related diseases in mammals.

In step 25, the phenolic compound 18 reacts with the carboxylic acid 6 in dichloromethane in the presence of 1 equivalent amount of dicyclohexylcarbodiimide (DCC) and 4-dimethylaminopyridine (DMAP), giving the ester 30.

The same reaction takes place in step 26 between compounds 22 and 6, giving the ester 31.

Compounds 30 and 31 are among the group of preferred isoxazolidinedione analogs that have therapeutic properties against NIDDM and related diseases in mammals.

Ethyl acetoacetate 32 undergoes the same chemical treatment in steps 27 to 29 as acetylacetone 7 in steps 6 to 9 (FIG. 3). Thus, compound 32 in glacial acetic acid reacts with sodium nitrite, and the resulting oxime intermediate is not isolated but is reduced with zinc powder in acetic acid to give the amine 33. The amine is then coupled with benzoyl chloride in dichloromethane in the presence of triethylamine. The resulting benzamide 34 is then cyclized with a catalytic amount of sulfuric acid in refluxing ethyl acetate, giving the substituted oxazole 35.

In step 30, the ethyl carboxylate function of compound 35 is reduced with lithium aluminum hydride in THF to give the primary alcohol 36 (an analog of compounds 12 and 13).

In step 31, the ethyl carboxylate function of compound 35 is hydrolyzed in 6N HCl to give the carboxylic acid 37 (an analog of compound 6).

It should be understood that the reaction schemes and embodiments described herein are for illustrative purposes only and that various modifications or changes in light thereof will be suggested to persons skilled in the art and are to be included within the spirit and purview of this application and the scope of the appended claims.

EXAMPLE 1
CYP Assays

A series of assays to test for activity of 5 principal drug metabolizing enzymes, CYP1A4, CYP2C9, CYP2C19, CYP2D6, and CYP3A4, as well as other CYP450 subfamilies, have been designed and are now commercially available either as ready-to-use kits or as contract work. Commercial sources for these assays include for example Gentest and MDS Panlabs. These assays can test for activity of the enzyme toward metabolism of the test compound as well as testing for kinetic modification (inhibition or activation) of the enzyme by the substrate. These in vitro protocols use simple rapid, low cost methods to characterize aspects of drug metabolism and typically require less than 1 mg of test material.

EXAMPLE 2
High Throughput Cytochrome P450 Inhibition Screen

The majority of drug-drug interactions are metabolism-based and of these, most involve CYP450. For example, if a new chemical entity is a potent CYP450 inhibitor, it may inhibit the metabolism of a co-administered medication, potentially leading to adverse clinical events. The inhibition of human CYP1A2, CYP2C8, CYP2C9, CYP2C19, CYP2D6, CYP3A4 and other isoforms are assessed using microsomal preparations as enzyme sources and the fluorescence detection method described in the literature (Crespi, C. L., et al. (1997) Microtiter plate assays for inhibition of human, drug-metabolizing cytochromes P450. Anal. Biochem. 248:188–190; Crespi, C. L., et al. (1999) Novel High throughput fluorescent cytochrome P450 assays. Toxicol. Sci. 48, abstr. No. 323; Favreau, L. V., et al. (1999) Improved Reliability of the Rapid Microtiter Plate Assay Using Recombinant Enzyme in Predicting CYP2D6 Inhibition in Human Liver Microsomes. Drug Metab. Dispos. 27:436–439). Tests are conducted in 96-well microtiter plates and may use the following fluorescent CYP450 substrates: resorufin benzyl ether (BzRes), 3-cyano-7-ethoxycoumarin (CEC), ethoxyresorufin (ER), 7-methoxy-4-trifluoromethylcoumarin (MFC), 3-[2-(N,N-diethyl-N-methylamino)ethyl]-7-methoxy-4-methylcoumarin (AMMC), 7-benzyloxy-quinoline (BQ), dibenzyfluorescein (DBF) or 7-benzyloxy-4-trifluoromethylcoumarin (BFC). Multiple CYP3A4 substrates are available to assess substrate dependence of $IC_{50}$ values, activation and the complex inhibition kinetics associated with this enzyme (Korzekwa, K. R., et al. (1998). Evaluation of atypical cytochrome P450 kinetics with two-substrate models: evidence that multiple substrates can simultaneously bind to the cytochrome P450 active sites. Biochemistry., 37, 4137–4147; Crespi, C. L. (1999) Higher-throughput screening with human cytochromes P450. Curr. Op. Drug Discov. Dev.2: 15–19). Data are reported as $IC_{50}$ values or percent inhibition when using only one or two concentrations of test compound.

EXAMPLE 3
Metabolic Stability

Metabolic stability influences both oral bioavailability and half-life; compounds of higher metabolic stability are less controllable in their pharmacokinetic parameters. This combination of characteristics, or properties, leads to potential DDI and liver toxicity. This test measures the metabolic stability of the compound in the presence of CYP450, in the presence of hydrolytic enzymes, and in the presence of both CYP450 and hydrolytic enzymes.

Stability in the Presence of CYP450: With CYP450 substrates of low and moderate in vivo clearance, there is a good correlation between in vitro metabolic stability and in vivo clearance (Houston, J. B. (1994) Utility of in vitro drug metabolism data in predicting in vivo metabolic clearance). This test uses pooled liver microsomes, S9 (human and/or preclinical species) or microsomal preparations with appropriate positive and negative controls. Assessment of both phase-I and phase-II enzymatic metabolism is possible, and a standard set of substrate concentrations and incubations may be used. Metabolism is measured by loss of parent compound HPLC analysis with absorbance, fluorescence, radiometric or mass spectrometric detection can be used.

Stability in the Presence of Hydrolytic Enzymes: Hydrolytic enzymes in liver cytosol, plasma, or enzymatic mixes from commercial sources (human and/or preclinical species) are used to assess the metabolic stability of the novel compounds of the invention. Appropriate positive and negative controls, as well as a standard set of substrate concentrations, are added in order to correlate in vitro observations with in vivo metabolic half-life. Metabolism is measured by loss of parent compound. HPLC analysis with absorbance, fluorescence, radiometric or mass spectrometric detection can also be used.

Stability in the Presence of both CYP450 and Hydrolytic Enzymes: This test uses pooled liver microsomes, S9 (human and/or preclinical species) or microsomal preparations with appropriate positive and negative controls, combined with hydrolytic enzymes from commercial sources, plasma, or cytosol to assess metabolic stability. The test can also be performed in primary hepatocytes (human and/or preclinical species) or in perfused liver (preclinical species). The use of positive and negative controls, as well as a standard set of substrates allow for correlations between in vitro observations and in vivo metabolic half-life.

EXAMPLE 4
CYP1A1 Induction Screening

Induction of CYP1A1 is indicative of ligand activation of the aryl hydrocarbon (Ah) receptor, a process associated with induction of a variety of phase-I and phase-II enzymes (Swanson, H. I. (1993) The AH-receptor: genetics, structure and function. Pharmacogenetics 3:213–230). Many pharmaceutical companies choose to avoid development of compounds suspected as Ah-receptor ligands. This test uses a human lymphoblastoid cell line containing native CYP1A1 activity that is elevated by exposure to Ah receptor ligands. Assays are conducted in 96-well microtiter plates using an overnight incubation with the test substances, followed by addition of 7-ethoxy-4-trifluoromethylcoumarin as substrate. Dibenz(a,h)anthracene is used as a positive control inducer. A concurrent control test for toxicity or CYP1A1 inhibition is available using another cell line that constitutively expresses CYP1A1.

EXAMPLE 5
Cytochrome P450 Reaction Phenotyping

The number and identity of CYP450 enzymes responsible for the metabolism of a drug affects population variability in metabolism. Reaction phenotyping uses either liver microsomes with selective inhibitors or a panel of cDNA-expressed enzymes to provide a preliminary indication of the number and identity of enzymes involved in the metabolism of the substrate. The amount of each cDNA-expressed enzyme is chosen to be proportional to the activity of the same enzyme in pooled human liver microsomes. Protein concentration is standardized by the addition of control microsomes (without CYP450 enzymes). A standard set of substrate concentrations and incubations is used and metabolism of the drug is measured by loss of parent compound. Alternatively, HPLC analysis with absorbance, fluorescence, radiometric or mass spectrometric detection can be used.

EXAMPLE 6
Drug Permeability Measurement in Caco-2, LLC-PK1 or MDCK Cell Monolayers Drug permeability through cell monolayers correlates well with intestinal permeability and oral bioavailability. Several mammalian cell lines are appropriate for this measurement (Stewart, B. H., et al. (1995) Comparison of intestinal permeabilities determined in multiple in vitro and in situ models: relationship to absorption in humans. Pharm. Res. 12:693–699; Irvine, J. D., et al. (1999). MDCK (Madin-Darby Canine Kidney) cells: A tool for membrane permeability screening. J. Pharm. Sci. 88:28–33). Apical to basolateral diffusion is measured using a standard set of time points and drug concentrations. These systems can be adapted to a high throughput mode. Liquid chromatography/mass spectroscopy (LC/MS) analysis is also available for analysis of metabolites. Controls for membrane integrity and comparator compounds are included and data are reported as apparent permeability ($P_{app}$) or percent flux under fixed conditions.

EXAMPLE 7
Human P-glycoprotein (PGP) Screen

An ATPase assay is used to determine if the compounds interact with the xenobiotic transporter MDR1 (PGP). ATP hydrolysis is required for drug efflux by PGP, and the ATPase assay measures the phosphate liberated from drug-stimulated ATP hydrolysis in human PGP membranes. The assay screens compounds in a high throughput mode using single concentration determinations compared to the ATPase activity of a known PGP substrate. A more detailed approach by determining the concentration-dependence and apparent kinetic parameters of the drug-stimulated ATPase activity, or inhibitory interaction with PGP can also be used.

EXAMPLE 8
PGP-Mediated Drug Transport in Polarized Cell Monolayers

P-glycoprotein (PGP) is a member of the ABC transporter superfamily and is expressed in the human intestine, liver and other tissues. Localized to the cell membrane, PGP functions as an ATP-dependent efflux pump, capable of transporting many structurally unrelated xenobiotics out of cells. Intestinal expression of PGP may affect the oral bioavailability of drug molecules that are substrates for this transporter. Compounds that are PGP substrates can be identified by direct measurement of their transport across polarized cell monolayers. Two-directional drug transport (apical to basolateral permeability, and basolateral to apical PGP-facilitated efflux) can be measured in LLC-PK1 cells (expressing human PGP cDNA) and in corresponding control cells. Caco-2 cells can also be used. Concentration-dependence is analyzed for saturation of PGP-mediated transport, and apparent kinetic parameters are calculated. Test compounds can also be screened in a higher throughput mode using this model. LC/MS analysis is available. Controls for membrane integrity and comparator compounds are included in the assay system.

EXAMPLE 9
Protein Binding

LC/MS analysis can be used to assess the affinity of the test compound for immobilized human serum albumin (Tiller, P. R., et al. (1995) Immobilized human serum albumin: Liquid chromatography/mass spectrometry as a method of determining drug-protein binding. Rapid comm. mass spectrom. 9:261–263). Appropriate low, medium and high binding positive control comparators are included in the test.

EXAMPLE 10
Metabolite Production

Milligram quantities of metabolites can be produced using microsomal preparations or cell lines. These metabolites can be used as analytical standards, an aid in structural characterization, or as material for toxicity and efficacy testing.

EXAMPLE 11
Effect on Herg Channel

This assay tests the effect of parent drugs and metabolite(s) on Herg channels using either a cloned Herg channel expressed in stable human embryonic kidney cells (HEK), or Chinese hamster ovary cells (CHO) transiently expressing the Herg/MiRP-1-encoded potassium channel. Whole cell experiments are carried out by means of the patch-clamp technique and performed in the voltage-clamp mode.

In the test using HEK cells, cells are depolarized from the holding potential of −80 mV to voltages between −80 and +60 mV in 10 mV increments for 4 seconds in order to fully open and inactivate the channels. The voltage is then stepped back to −50 mV for 6 seconds in order to record the tail current. The current is also recorded in the presence of test compounds in order to evaluate a dose-response curve of the ability of a test compound to inhibit the Herg channel.

In the test involving CHO cells, the cells are clamped at a holding potential of −60 mV in order to establish the whole-cell configuration. The cells are then depolarized to +40 mV for 1 second and afterwards hyper-/depolarized to potentials between −120 and +20 mV in 20 mV increments for 300 mSec in order to analyze the tail currents. To investigate the effects of test compounds, the cells are depolarized for 300 mSec to +40 mV and then repolarized to −60 mV at a rate of 0.5 mV/mSec, followed by a 200-mSec test potential to −120 mV. After 6 control stimulations, the extracellular solution is changed to a solution containing the test compound, and 44 additional stimulations are then performed. The peaks of the outward currents and inward tail currents are analyzed.

Activity on HERG channel can also be assessed using a perfused heart preparation, usually guinea pig heart or other small animal. In this assay the heart is paced and perfused with a solution containing a known concentration of the drug. A concentration-response curve of the effects of drug on QT interval is then recorded and compared to a blank preparation in which the perfusate does not contain the drug.

EXAMPLE 12
Toxicity in Hepatocyte Cell Culture

This test is performed in primary human and porcine hepatocyte cultures. Toxicity is determined by the measurement of total protein synthesis by pulse-labeling with [$^{14}$C] leucine (Kostrubsky, V. E., et al. (1997) Effect of taxol on cytochrome P450 3A and acetaminophen toxicity in cultured rat hepatocytes: Comparison to dexamethasone. Toxicol. Appl. Pharmacol. 142:79–86), and by reduction of 3-(4,5-dimethylthiazol-2-yl)-2,5-diphenyltetrazolium bromide using a protocol described by the manufacturer (Sigma Chemical Co., St. Louis, Mo.). Hepatocytes can be isolated from livers not used for whole organ transplants or from male Hanford miniature pigs.

We claim:

1. A compound comprising

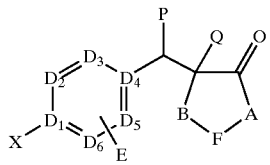
Formula I wherein:

A is N11 and B is C=O or;

F is O;

$D_1$–$D_6$ are C;

E is 11;

P and Q can be a double bond or H;

X is

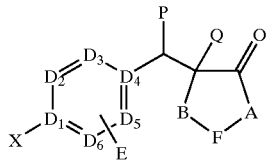

and analogs, derivatives, or salts of the compound of Formula I.

2. A composition comprising a carrier and a compound comprising

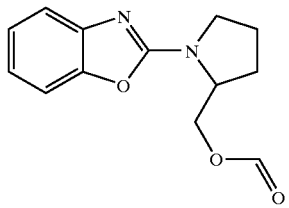
Formula I wherein:

A is N11 and B is C=O;

F is O;

$D_1$–$D_6$ are C;

E is 11;

P and Q can be a double bond or H;

X is

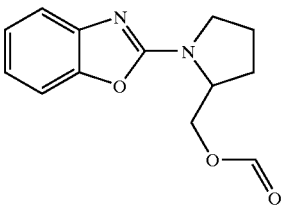

and analogs, derivatives, or salts of the compound of Formula I.

3. The composition according to claim 2, wherein said carrier is a pharmaceutically acceptable carrier.

4. A method of treating diabetes, atherosclerosis, hypercholesterolemia, or hyperlipidemia comprising the administration of a therapeutically effective amount of the composition comprising a carrier and a compound comprising

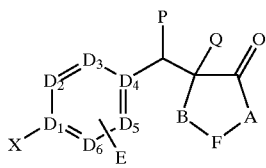
Formula I wherein:

A is N11 and B is C=O;

F is O;

$D_1$–$D_6$ are C;

E is 11;

P and Q can be a double bond or H;

X is

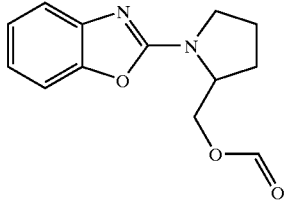

and analogs, derivatives, or salts of the compound of Formula I.

5. The method according to claim 4, wherein said carrier is a pharmaceutically acceptable carrier.

* * * * *

UNITED STATES PATENT AND TRADEMARK OFFICE
CERTIFICATE OF CORRECTION

PATENT NO. : 6,784,199 B2
DATED : August 31, 2004
INVENTOR(S) : Pascal Druzgala and Peter G. Milner It is certified that error appears in the above-identified patent and that said Letters Patent is hereby corrected as shown below:

Column 2,
Line 42, "a carboys" should read -- acarbose --

Column 5,
Lines 41-42, "the subject invention provides compounds have" should read -- the subject invention provides compounds having --
Line 48, "the subject invention provides compounds have" should read -- the subject invention provides compounds having --

Column 10,
Lines 10 and 44, "heterocloalkyl" should read -- heterocycloalky --
Lines 29 and 40, "akynyl" should read -- alkynyl --

Line 60, " 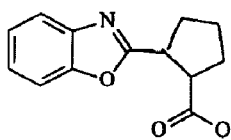 " should read -- 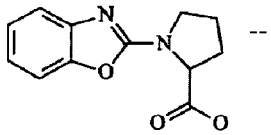 --

Column 12,
Lines 38-39, "rat, pig, horse, rabbit, goat, pig, cow, cat, dog, or human." should read -- rat, pig, horse, rabbit, goat, cow, cat, dog, or human. --

Column 14,
Line 22, "isoxalolidinedione" should read -- isoxazolidinedione --

Column 15,
Line 41, "dibenzyfluorescein" should read -- dibenzylfluorescein --
Line 49, "Biochemistry.," should read -- Biochemistry, --

UNITED STATES PATENT AND TRADEMARK OFFICE
CERTIFICATE OF CORRECTION

PATENT NO. : 6,784,199 B2
DATED : August 31, 2004
INVENTOR(S) : Pascal Druzgala and Peter G. Milner It is certified that error appears in the above-identified patent and that said Letters Patent is hereby corrected as shown below:

Column 19,
Line 15, "A is N11" should read -- A is NH --
Line 19, "E is 11" should read -- E is H --

Signed and Sealed this

Twenty-fifth Day of January, 2005

JON W. DUDAS
*Director of the United States Patent and Trademark Office*

UNITED STATES PATENT AND TRADEMARK OFFICE
CERTIFICATE OF CORRECTION

PATENT NO. : 6,784,199 B2
DATED : August 31, 2004
INVENTOR(S) : Pascal Druzgala and Peter G. Milner It is certified that error appears in the above-identified patent and that said Letters Patent is hereby corrected as shown below:

Column 5,
Line 48, please replace "Another embodiment provides compounds have" with
-- Another embodiment provides compounds having --.

Column 10,
Lines 10 and 44, please replace "heteroycloalkyl" with -- heterocycloalkyl --.

Column 19,
Line 49, please replace "A is N11" with -- A is NH --.
Line 52, please replace "E is 11" with -- E is H --.

Column 20,
Line 32, please replace "A is N11" with -- A is NH --.
Line 35, please replace "E is 11" with -- E is H --.

Signed and Sealed this

Twelfth Day of July, 2005

JON W. DUDAS
*Director of the United States Patent and Trademark Office*